United States Patent
Nishizaki (10) Patent No.: US 9,655,911 B2
(45) Date of Patent: May 23, 2017

(54) ANTIDEPRESSANT COMBINATION DRUG

(71) Applicant: NISHIZAKI BIOINFORMATION RESEARCH INSTITUTE, Kobe-shi, Hyogo (JP)

(72) Inventor: Tomoyuki Nishizaki, Kobe (JP)

(73) Assignee: Nishizaki Bioinformation Research Institute, Kobe (JP)

( * ) Notice: Subject to any disclaimer, the term of this patent is extended or adjusted under 35 U.S.C. 154(b) by 0 days.

(21) Appl. No.: 15/029,885

(22) PCT Filed: Oct. 14, 2014

(86) PCT No.: PCT/JP2014/077351
§ 371 (c)(1),
(2) Date: Apr. 15, 2016

(87) PCT Pub. No.: WO2015/056675
PCT Pub. Date: Apr. 23, 2015

(65) Prior Publication Data
US 2016/0235773 A1    Aug. 18, 2016

(30) Foreign Application Priority Data
Oct. 15, 2013    (JP) .................... 2013-214475

(51) Int. Cl.
*A61K 31/685*    (2006.01)
*A23J 7/00*    (2006.01)

(52) U.S. Cl.
CPC .............. *A61K 31/685* (2013.01); *A23J 7/00* (2013.01); *A23V 2002/00* (2013.01)

(58) Field of Classification Search
None
See application file for complete search history.

(56) References Cited

U.S. PATENT DOCUMENTS

2009/0074857 A1    3/2009 Dror et al.
2013/0274228 A1*    10/2013 Nishizaki .............. A23L 1/3006
                                                  514/77

FOREIGN PATENT DOCUMENTS

JP    2007-022965 A    2/2007
JP    2009-007329 A    1/2009
(Continued)

OTHER PUBLICATIONS

Kanno et al., Behavioral Pharmacology, 25(5&6): 575-581 (2014).*
(Continued)

*Primary Examiner* — Karl J Puttlitz
(74) *Attorney, Agent, or Firm* — Leydig, Voit & Mayer, Ltd.

(57) ABSTRACT

The combined use of 1,2-dilinoleoyl-sn-glycero-3-phosphocholine and 1-palmitoyl-2-oleoyl-sn-glycero-3-phosphocholine affords a superior anti-depressive action, an improving effect on the cognitive function associated with depression, an improving effect on the stress-induced suppression of Akt activation, and a suppressive action on the stress-induced GSK-3β activation. Therefore, the present invention can provide an antidepressant combination drug, an agent for improving cognitive function associated with depression, an agent for improving stress-induced suppression of Akt activation and an agent for suppressing stress-induced GSK-3β activation.

4 Claims, 3 Drawing Sheets (56) References Cited

FOREIGN PATENT DOCUMENTS

JP      2011-525525 A        9/2011
WO      2012090713      *    7/2012

OTHER PUBLICATIONS

Kanno et al., "DL-/PO-phosphatidylcholine restores restraint stress-induced depression-related behaviors and spatial memory impairment," *Behavioral Pharmacology*, 25(5&6): 575-581 (2014).

Nagata et al., "DL- and PO-phosphatidylcholines as a promising learning and memory enhancer," *Lipids in Health and Disease*, 10: 25 (Jan. 28, 2011).

* cited by examiner

ANTIDEPRESSANT COMBINATION DRUG

CROSS-REFERENCE TO RELATED APPLICATIONS

This patent application is the U.S. national phase of International Patent Application No. PCT/JP2014/077351, filed Oct. 14, 2014, which claims the benefit of Japanese Patent Application No. 2013-214475, filed on Oct. 15, 2013, which are incorporated by reference in their entireties herein.

TECHNICAL FIELD

The present invention relates to an antidepressant combination drug. More particularly, the present invention relates to a combined use of two kinds of phosphatidylcholine for the treatment of depression, and for the improvement of cognitive function associated with depression.

BACKGROUND ART

While depression is a general disease among mental diseases, since diagnosis is often overlooked and a treatment is not performed, the morbidity rate is high and the patients fall into social-psychological maladjustment. Depression can be mainly classified into a bipolar disease showing radical mood changes, major depression characteristically showing severe depression state but unaccompanied by manic state, and bipolar disorderase and major depression which is more uncertain and mild and does not satisfy a particular diagnosis standard (e.g., dysthymic disorder).

As medicaments effective for the treatment of depression, tricyclic antidepressants (TCA), selective serotonin reuptake inhibitors (SSRI), and monoamine oxidase inhibitors (MAOI) can be mentioned, and many of them increase utilizability of catecholamine (noradrenaline and dopamine) and indoleamine (serotonin) in the central nervous system (CNS). The clinical effectiveness of these medicaments has produced catecholamine-indoleamine hypothesis of depression, and the drug treatment of depression at present is based on this hypothesis.

However, for example, TCA causes side effects, and therefore, EKG and plasma drug concentrations need to be monitored. An adverse influence of SSRI on the sex function (mainly anorgasmia and delayed ejaculation) has been reported. Other general side effects include extrapyramidal-like side effects such as sleep disorder, yawn, changes in body weight, suicidal ideation, dystonic reaction and the like.

Thus, the development of a new therapeutic drug for depression, which does not show harmful side effects that existing medicaments show, but affords an improved effect, has been desired.

On the other hand, the present inventor has reported that phosphatidylcholine shows a cognitive function-improving effect, and a combined use of two particular kinds of phosphatidylcholine is more effective for the improvement of cognitive function (patent document 1). However, it is not known that a combined use of two particular kinds of phosphatidylcholine exhibits a superior anti-depressive action.

DOCUMENT LIST

Patent Documents patent document 1: JP-A-2009-7329

SUMMARY OF THE INVENTION

Problems to be Solved by the Invention

The present invention aims to provide an antidepressant combination drug and the like.

Means of Solving the Problems

The present inventor has found from previous studies that a combined use of two particular kinds of phosphatidylcholine is more effective for the improvement of the cognitive function.

During the process of various studies relating to the combined use, the present inventor has surprisingly found that a combined use of two particular kinds of phosphatidylcholine, namely, 1,2-dilinoleoyl-sn-glycero-3-phosphocholine (DL-PC) and 1-palmitoyl-2-oleoyl-sn-glycero-3-phosphocholine (PO-PC), has an action to improve suppression of Akt activation, which is induced by stress (hereinafter stress-induced suppression of Akt activation), and to suppress GSK-3β activation induced by stress (hereinafter stress-induced GSK-3β activation), and further, a superior anti-depressive action, and a depression-associated cognitive function-improving effect, which resulted in the completion of the present invention. Accordingly, the present invention is as described below.

(1) An antidepressant combination drug comprising DL-PC and PO-PC.
(2) The drug of the above-mentioned (1), which is a food.
(3) An agent for improving stress-induced suppression of Akt activation, comprising DL-PC and PO-PC.
(4) An agent for suppressing stress-induced GSK-3β activation comprising DL-PC and PO-PC.
(5) The agent of the above-mentioned (3) or (4), which is a reagent for study.
(6) A method for the prophylaxis, improvement and/or treatment of depression, comprising administering an effective amount of DL-PC and an effective amount of PO-PC in combination to a target in need thereof.
(7) A method of improving stress-induced suppression of Akt activation, comprising treating cells or tissues with DL-PC and PO-PC.
(8) A method of suppressing stress-induced GSK-3β activation, comprising treating cells or tissue with DL-PC and PO-PC.

Effect of the Invention

The combined use of DL-PC and PO-PC affords an action to improve stress-induced suppression of Akt activation and an action to suppress stress-induced GSK-3β activation, and is useful as various reagents (agents) for study based on the actions thereof, as well as an antidepressant combination drug and an agent for improving cognitive function associated with depression.

BRIEF DESCRIPTION OF THE DRAWINGS

FIG. 4 is a graph showing that the combined use of DL-PC and PO-PC administration improves stress-induced dephosphorylation of GSK-33. A restraint stress was loaded to mice for 4 days, after which DL-PC and PO-PC, or polyethylene glycol (PEG) was orally administered for 3 days, and a forced swimming test was performed. The mice were then used for the experiment. In the graph, each column shows mean value (±SEM) of Ser9 phosphorylated GSK-3β (pS9) relative to the total GSK-3β (n=4 in each experiment). P value, Dunnett's test. DL-/PO-PC: DL-PC and PO-PC

FIG. 5 is a graph showing that the combined use of DL-PC and PO-PC administration improves stress-induced dephosphorylation of Akt. A restraint stress was loaded to mice for 4 days, after which DL-PC and PO-PC, or polyethylene glycol (PEG) was orally administered for 3 days, and a forced swimming test was performed. The mice were then used for the experiment. In the graph, each column shows mean value (±SEM) of phosphorylated Akt relative to the total Akt (n=4 in each experiment). P value, Dunnett's test. NS, not significant. DL-/PO-PC: DL-PC and PO-PC

DESCRIPTION OF EMBODIMENTS

The present invention is explained in detail in the following.

The present invention is characterized by the use of two kinds of particular phosphatidylcholines in combination. In the present specification, the present invention using the two kinds of phosphatidylcholine in combination is also conveniently referred to as the combination drug of the present invention.

One of the phosphatidylcholines is dilinoleoyl phosphatidylcholine represented by the following formula wherein —C(O)R$_1$ and —C(O)R$_2$ are each a linoleic acid residue, (1,2-dilinoleoyl-sn-glycero-3-phosphocholine; DL-PC).

The other phosphatidylcholine is palmitoyloleoyl phosphatidylcholine represented by the following formula wherein —C(O)R$_3$ is a palmitic acid residue, and —C(O)R$_4$ is an oleic acid residue, (1-palmitoyl-2-oleoyl-sn-glycero-3-phosphocholine; PO-PC).

The DL-PC and PO-PC may be derivatized in view of the activity and safety thereof. For example, derivatizations such as hydrogenation, hydroxylation, alkylation, halogenation and the like can be mentioned, but are not limited thereto.

The DL-PC and PO-PC to be used in the present invention are not particularly limited and include those isolated and purified from animals (egg-yolk and the like), plants (soybean and the like), fungi (yeast, mold) and the like, those synthesized chemically and the like. In addition, the DL-PC and PO-PC to be used in the present invention can be used without any particular limitation as long as they have been purified to the level permitting use as a medicament. Furthermore, a commercially available product can also be used.

The amount of each of DL-PC and PO-PC in the combination drug of the present invention varies depending on the administration form of the combination drug (as mentioned below), severity of the disease, the animal species to be the subject of administration, drug acceptability, body weight and age of the subject of administration, and the like. Generally, 50-500 mg, preferably 100-300 mg, of DL-PC and 50-500 mg, preferably 100-300 mg, of PO-PC are administered per day to an adult subject. The ingestion ratio of DL-PC and PO-PC is preferably about 1:1. The dose of DL-PC and PO-PC can be decreased when they are used in combination than when they are used singly.

The administration form of the combination drug of the present invention is not particularly limited and DL-PC and PO-PC only need to be combined at the time of administration. Examples of such administration form include (1) administration as a single preparation obtained by simultaneously formulating DL-PC and PO-PC, (2) simultaneous administration of two kinds of preparations obtained by separately formulating DL-PC and PO-PC, by the same administration route, (3) administration of two kinds of preparations obtained by separately formulating DL-PC and PO-PC, in a staggered manner by the same administration route, (4) simultaneous administration of two kinds of preparations obtained by separately formulating DL-PC and PO-PC, by different administration routes, (5) administration of two kinds of preparations obtained by separately formulating DL-PC and PO-PC, in a staggered manner by different administration routes, and the like.

From the aspect of convenience, administration as a single preparation and simultaneous administration of two kinds of preparations by the same route are preferable.

In the following, the "preparation" in the present invention includes both a single preparation obtained by simultaneously formulating DL-PC and PO-PC, and two kinds of preparations obtained by separately formulating DL-PC and PO-PC.

The combination drug of the present invention can contain any additive, for example, pharmaceutically acceptable carrier, besides the active ingredient, DL-PC and PO-PC. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyllysin.ammonium salt, glycine, orange powder and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline, orange juice and the like, base waxes such as cacao butter, polyethylene glycol, paraffin and the like, and the like.

In one embodiment, the combination drug of the present invention can be formulated as a preparation preferable for oral administration. The preparation preferable for oral administration includes a liquid wherein an effective amount of a substance is dissolved in a diluent such as water and saline, a capsule, granule, powder or tablet, containing an effective amount of a substance as a solid or granule, a suspension wherein an effective amount of a substance is suspended in a suitable dispersing medium, an emulsion wherein a solution containing an effective amount of a substance dissolved therein is dispersed and emulsified in a suitable dispersing medium, and the like.

In another embodiment, the combination drug of the present invention can be formulated as a preparation preferable for parenteral administration. The preparation preferable for parenteral administration (e.g., intravenous injection, subcutaneous injection, intramuscular injection, topical injection and the like) includes aqueous and non-aqueous isotonic sterile injection liquids, which may contain antioxidant, buffer, bacteriostatic agent, isotonicity agent and the like. Aqueous and non-aqueous sterile suspensions can also be mentioned, which may contain suspending agent, solubilizer, thickener, stabilizer, preservative and the like. Such preparation can be sealed in a container such as ampoule and vial by a unit dose or plural doses. In addition, it is also possible to freeze-dry the active ingredient and pharmaceutically acceptable carriers, and preserve them in a suitable sterile vehicle in a state only requiring dissolving or suspending immediately before use.

The combination drug of the present invention containing DL-PC and PO-PC as the active ingredients has an anti-depressive action an action to improve cognitive function associated with depression in mammals (e.g., mouse, rat, hamster, rabbit, cat, dog, bovine, sheep, monkey, human and the like). Therefore, the combination drug of the present invention containing DL-PC and PO-PC is useful for treatment of depression (antidepressant combination drug), and an agent for improving cognitive dysfunction associated with depression, and is provided as a pharmaceutical product (hereinafter sometimes to be simply referred to as the medicament of the present invention). In addition, because of such pharmacological action by the combined use of DL-PC and PO-PC as an active ingredient, the present invention can provide a method for the prophylaxis, improvement and/or treatment of depression (hereinafter to be also simply referred to as the method of the present invention).

When used in the present specification, the "treatment" means reducing or preventing or delaying worsening of depression symptom in a test subject (target) showing such symptoms. The "improvement" means improving cognitive impairment associated with depression, preferably improving to the level permitting normal daily life, in a test subject (target) showing such symptoms. The "prophylaxis" means prevention of manifestation of depression in a test subject (target) showing no such symptoms.

The combination drug of the present invention can be provided as a food. The combination drug of the present invention containing DL-PC and PO-PC as active ingredients has an anti-depressive action and action to improve cognitive function associated with depression in mammals (e.g., mouse, rat, hamster, rabbit, cat, dog, bovine, sheep, monkey, human and the like). Therefore, the combination drug of the present invention containing DL-PC and PO-PC as active ingredients is effective for the prophylaxis or improvement of depression and cognitive functional impairment associated with depression. Particularly, the combination drug can be provided as a functional food effective for the prophylaxis or improvement of depression and cognitive functional impairment associated with depression.

The "food" in the present invention means any food and drink other than pharmaceutical products and quasi-drugs. For example, it includes, but is not limited to, foods for specified health uses, foods with nutrient function claims, and so-called supplements.

When the combination drug of the present invention is used as a food, the food includes, for example, general foods (e.g., bread, milk product (e.g., milk, yoghurt), confectionery, candy, drop, chocolate, cake, pudding, jelly, soft drink, noodles), health foods, dietary supplements, and foods for specified health uses and foods with nutrient function claims, which are defined in the food with health claims system by the Ministry of Health, Labour and Welfare. The foods can be in any form such as liquid (water-soluble, insoluble), solid such as powder, granule, tablet, capsule and the like, semi-sold such as jelly etc. and the like. The combination drug of the present invention can be used by dissolving in water or a predetermined aqueous solution. In this case, the combination drug of the present invention may contain a solubilizing agent (e.g., linoleic acid) and a stabilizer.

When the combination drug of the present invention is used as a food, the amount thereof to be ingested varies depending on the form of use (e.g., liquid, solid, semi-solid), concentration of DL-PC and PO-PC contained, presence or absence, the kind and amount of a component to be contained besides DL-PC and PO-PC, and the like, and cannot be generalized. Normally, DL-PC and PO-PC are preferably contained in a food in a total amount of not less than 30%, more preferably not less than 90%. Examples of the components other than DL-PC and PO-PC in the food include the above-mentioned optional additives.

The combination drug of the present invention may be in a form wherein a unit ingestion amount or a portion thereof is individually packed or filled, or the unit ingestion amount or a portion thereof in a large number are comprehensively packed or filled.

When the combination drug of the present invention is provided as a single preparation, the unit ingestion amount or a portion thereof is the unit ingestion amount or a portion thereof of the total amount of DL-PC and PO-PC, that is, the total phosphatidylcholine. When the combination drug of the present invention is provided for a combined use of two kinds of preparations, the unit ingestion amount or a portion thereof of the combination drug is a combination of the unit ingestion amount or a portion thereof of DL-PC, and the unit ingestion amount or a portion thereof of PO-PC.

Examples of the pharmaceutical product or a food wherein a unit ingestion amount or a portion thereof is individually packed or filled, those wherein a unit ingestion amount or a portion thereof is individually packed or filled in a general package (e.g., PTP (press through packing) sheet, paper container, film (e.g., plastic film) container, glass container, plastic container). Such pharmaceutical product or food individually packed or filled as above may be further combined and simultaneously packed or filled in one container (e.g., paper container, film (e.g., plastic film) container, glass container, plastic container). Examples of the pharmaceutical product or food wherein the unit ingestion amount or a portion thereof in a large number are comprehensively packed or filled include those wherein many tablets and capsules are packed or filled without sorting in one container (e.g., paper container, film (e.g., plastic film) container, glass container, plastic container). The pharmaceutical product or food of the present invention can also contain the unit ingestion amount or a portion thereof in a number sufficient for a long-term ingestion. In the case of a food, for example, in a number sufficient for 3 days or longer, preferably 7 days, 10 days, 14 days, 21 days or longer, or 1 month, 2 months, 3 months or longer.

The combination drug of the present invention may contain, in addition to DL-PC and PO-PC as essential active ingredients, other one or more kinds of compounds capable of treating or improving depression and cognitive functional impairment associated with depression.

As the pharmacological actions provided by the combined use of DL-PC and PO-PC, as clarified in the present invention, the following can be mentioned.

(1) Suppressive Action Against Stress-Induced GSK-3β Activation

There are a number of reports teaching that suppression of GSK-3β (GSK-3β phosphorylation) shows an antidepressive action (reference document). Phosphorylation of GSK-3β is suppressed by stress such as restraint stress and the like as shown in the below-mentioned Examples. The combined use of DL-PC and PO-PC not only inhibits suppression of such phosphorylation, but also promotes phosphorylation.

The combined use of DL-PC and PO-PC is useful as an antidepressant since an antidepressive action can be expected by suppression of stress-induced GSK-3β activation.

(Reference Document)
Latapy C, Rioux V, Guitton M J, Beaulieu J M. Selective deletion of forebrain glycogen synthase kinase 3β reveals a central role in serotonin-sensitive anxiety and social behaviour. Philos Trans R Soc Lond B Biol Sci 2012; 367(1601): 2460-2474.

(2) Action to Improve Stress-Induced Suppression of Akt Activation

Akt (also to be referred to as protein kinase B) is one kind of serine threonine phosphorylating enzyme, and activation thereof is considered to essentially require phosphorylation of two amino acids of threonine 308 group (Thr 308) and serine 473 group (Ser 473). Akt has a function to specifically phosphorylate serine or threonine residue of intracellular protein. For example, activated Akt inactivates GSK-3β by phosphorylating same.

Phosphorylation of Akt is suppressed by stress such as restraint stress and the like (i.e., activation of Akt is suppressed), which is as shown in the below-mentioned Examples. The combined use of DL-PC and PO-PC not only inhibits suppression of such phosphorylation, but also promotes phosphorylation.

The combined use of DL-PC and PO-PC is considered to suppress activation of GSK-3β by improving stress-induced suppression of Akt activation (reference documents). Therefore, the combined use of DL-PC and PO-PC could be useful as an antidepressant since an anti-depressive action can be expected.

(Reference Documents)
1. Leibrock C, Ackermann T F, Hierlmeier M, Lang F, Borgwardt S, Lang U E. Akt2 deficiency is associated with anxiety and depressive behavior in mice. Cell PhysiolBiochem 2013; 32:766-777.
2. Marsden W N. Synaptic plasticity in depression: molecular, cellular and functional correlates. Prog Neuropsychopharmacol Biol Psychiatry 2013; 43:168-184.

The combination drug of the present invention containing DL-PC and PO-PC as the active ingredients has an action to improve stress-induced suppression of Akt activation, and an action to suppress stress-induced GSK3β activation, in mammals (e.g., mouse, rat, hamster, rabbit, cat, dog, bovine, sheep, monkey, human and the like). Therefore, the combination drug of the present invention containing DL-PC and PO-PC is useful as an agent for improving stress-induced suppression of Akt activation, and an agent for suppressing stress-induced GSK-3β activation, and is provided as a reagent (hereinafter to be also referred to as the agent of the present invention).

A target cell or tissue to be treated with the agent of the present invention is not particularly limited as long as it is a cell or tissue capable of expressing active type Akt and active type GSK-3β. It is preferably a brain nerve cell derived from the above-mentioned mammal, and nerve cell model cell lines such as PC-12 cell line (adrenal gland medulla-derived pheochromocytoma) or mammal-derived brain tissue. As used herein, the "treatment" means contacting the above-mentioned cell or tissue with the agent of the present invention for a time necessary and sufficient. While the time varies depending on the desired effect and the kind of the cells to be used, it is generally 1 min-1 hr, preferably about 3-30 min. Conveniently, it is performed by incubation in a solution (e.g., culture medium) containing the agent of the present invention.

The contents disclosed in any publication cited in the present specification, including patents and patent applications, are hereby incorporated in their entireties by reference, to the extent that they have been disclosed herein.

While the present invention is explained in further detail in the following by referring to Examples, it is not limited by the following Examples and the like.

EXAMPLES (Experiment Method and Materials)
Handling Relating to Animals

All procedures have been approved by the Animal Care and Use Committee at Hyogo College of Medicine and are in compliance with NIH (the National Institute of Health) Guide for the Care and Use of Laboratory Animals.

Depression Model

At present, in the study of depression using the behavior of an experiment animal, the efficacy of antidepressant and reaction to stress, which are the both sides of depression, are mainly utilized. In a depression model, a method for inducing depression in an animal by imposing a stress such as solitude, electric shock, forced immersion in water, peripheral environment, temperature change and the like is mainly used. In this Experimental Example, a restraint stress animal model was used. A symptom corresponding to depression was induced by loading a stress by enclosing an experiment animal in a narrow space inhibiting movement, and whether an antidepression effect was observed when a test compound was administered was examined. Male C57BL/6J mouse at 8-week-old was purchased from Japan SLC Inc. (Shizuoka. Japan). The mouse was enclosed in a 11.5 cm plastic cylinder (diameter 2.7 cm) for 3 hr per day, which was performed for 4 consecutive days to impart a stress.

Forced Swimming Test

A forced swimming test is a behavioral test used for screening for an antidepression effect of a compound. Also in this Experimental Example, a restraint stress was loaded for 4 days, after which DL-PC and PO-PC, or polyethylene glycol (PEG) was orally administered for 3 days, and a forced swimming test was performed according to a previous report (Porsolt R D, Le Pichon M, Jalfre M. Depression: a new animal model sensitive to antidepressant treatments. Nature 1977; 266:730-732.). A mouse was placed in a plastic cylinder (height: 25 cm, diameter: 10 cm) filled with water to a height of 15 cm and left at 23° C. for 6 min. The time when the mouse floated without moving a hindpaw or swimming, which was observed in 4 min in the latter half, was measured as an immobility time and used as an index of a depression state.

Water Maze Test

Male Wister rats (7-week-old) were used for the water maze test. A circular plastic water tank (diameter 90 cm, depth 36 cm) was used. The inside of the water tank was completely painted in black, and dark water with India ink was filled up to 20 cm from the bottom (22° C.). A platform (diameter 11 cm) painted in black was placed in water such that it was 0.5 cm below the water surface. The water tank was placed in a test room, and several marks seen by the rat from the water tank were put thereon. During the test, the position of the marks was not changed. A platform was placed a predetermined position from the equal distance from the center and the end of the water tank, namely, center of one quadrant. At one of the randomly selected 5 points, the rat was released facing the wall of the water tank, and the time necessary for evacuating on the platform (acquisition latency) was measured. When smoothly evacuated, the rat was left on the platform for 10 seconds. When the rat failed to find the platform within 90 seconds, the test was stopped and the rat was left on the platform for 10 seconds. The test was performed at 2 min intervals, 4 times per day, for 4 consecutive days. After 7 days, the platform was removed, and the time necessary for reaching the place where the platform was once present (retention latency: 30 seconds at maximum) was measured.

Western Blotting

The proteins in the cytoplasm fraction, cellular membrane fraction and whole lysate were dissolved in 1% (w/v) sodium dodecyl sulfate. The proteins were separated by SDS-polyacrylamide gel electrophoresis using TGX gel (BioRad, Hercules, Calif., USA), and transferred on a polyvinylidene fluoride membrane. The blotting membrane was blocked with TBS-T [150 mM NaCl, 0.1% (v/v) Tween20 and 20 mM Tris, pH 7.5] containing 5% (w/v) BSA, and sequentially reacted respectively with the following antibodies.

Anti-phospho-threonine308-Akt(pThr308)antibody (Cell Signaling, Beverly, Mass., USA)
Anti-phospho-serine473-Akt(pSer473) antibody (Cell Signaling, Beverly, Mass., USA)
Anti-Akt antibody (Cell Signaling, Beverly, Mass., USA)
Anti-phospho-GSK-3β (pSer9) antibody (Cell Signaling, Beverly, Mass., USA)
Anti-GSK-3β antibody (Cell Signaling, Beverly, Mass., USA)

After washing, the membrane was reacted with horseradish peroxidase conjugated goat anti-rabbit IgG antibody or goat anti-mouse IgG antibody. The immunoreactivity was detected using ECL kit (Invitrogen, Carlsbad, Calif., USA), and visualized using a chemical luminescence detection system (GE Healthcare, Piscataway, N.J., USA). The signal density was measured by ImageQuant software (GE Healthcare).

(Results)

Experimental Example 1

Combined Use of DL-PC and PO-PC Improves Depression State in a Dose-Dependent Manner To mice made to develop a depression state by a restraint stress for 4 days was orally administered DL-PC and PO-PC, or polyethylene glycol (PEG) for 3 days. The mice were subjected to a forced swimming test, and the anti-depression effect of the combined use of DL-PC and PO-PC was examined by measuring the immobility time. As a positive control, mice free of a restraint stress were used, and PEG was used as a negative control.

Mice loaded with a restraint stress and those not loaded with a restraint stress were orally administered with DL-PC and/or PO-PC according to the following protocols (i)-(vi), by using an oral gavage needle once per day from the formation of the stress model to the completion of the test.

[Administration Protocol]
(i) combined use of DL-PC and PO-PC [DL-PC (0.05 mg/kg)+PO-PC (0.05 mg/kg), 0.1 mg/kg as PC]
(ii) the combined use of DL-PC and PO-PC [DL-PC (0.25 mg/kg)+PO-PC (0.25 mg/kg), 0.5 mg/kg as PC]
(iii) the combined use of DL-PC and PO-PC [DL-PC (0.5 mg/kg)+PO-PC (0.5 mg/kg), 1 mg/kg as PC]
(iv) the combined use of DL-PC and PO-PC [DL-PC (2.5 mg/kg)+PO-PC (2.5 mg/kg), 5 mg/kg as PC]
(v) DL-PC alone [1 mg/kg]
(vi) PO-PC alone [1 mg/kg]

Figure 1:
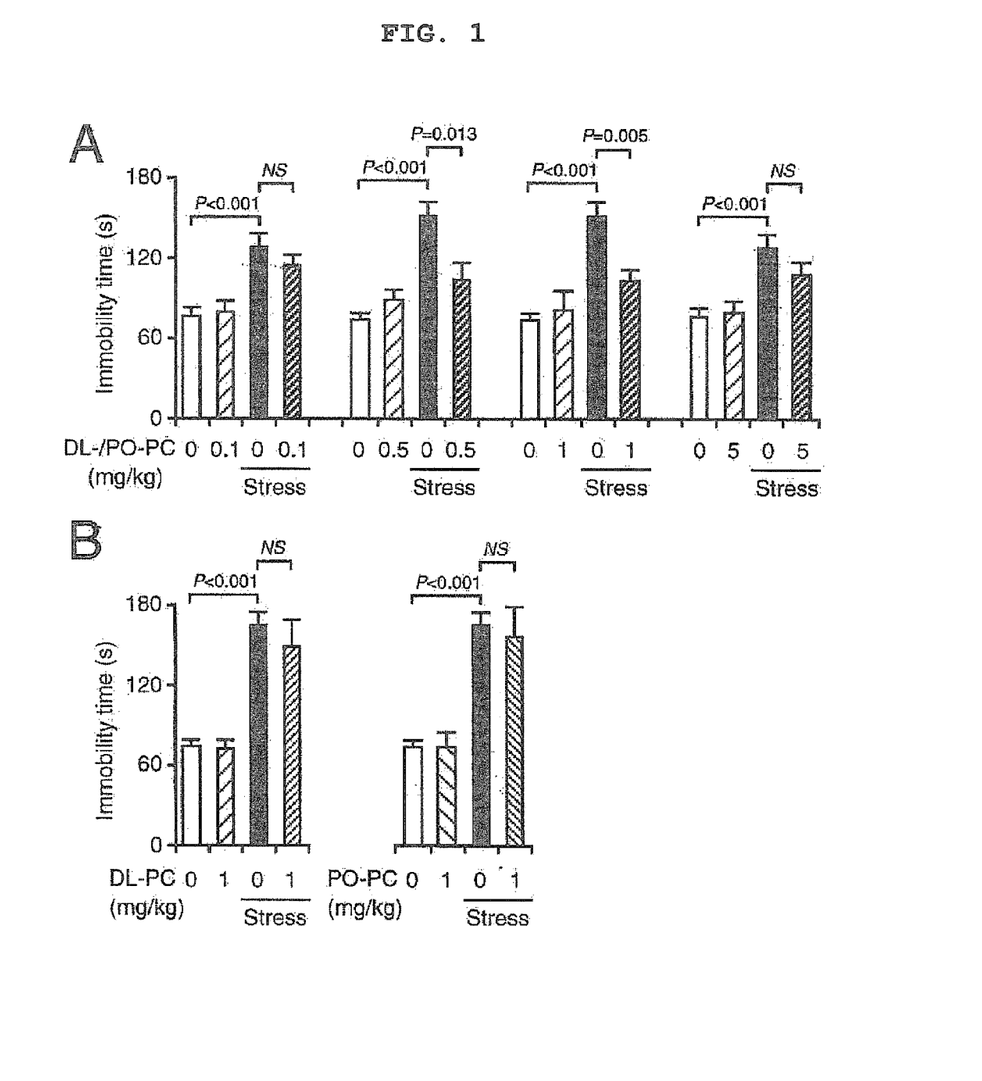
FIG. 1 is a graph showing that the combined administration of DL-PC and PO-PC improves, in a dose-dependent manner, an extended immobility time associated with stress-induced depression. A restraint stress was loaded for 4 days, after which DL-PC and PO-PC, or polyethylene glycol (PEG) was orally administered for 3 days, and a forced swimming test was performed. In the graph, each column shows mean value (±SEM) of immobility time (n=4-9 in each experiment). P value, Dunnett's test. NS, not significant. DL-/PO-PC: DL-PC and PO-PC

The results are shown in FIG. 1 [results of (i)-(iv): FIG. 1A, results of (v)-(vi): FIG. 1B]. It was clarified that the combined administration of DL-PC and PO-PC can improve a depression state due to a restraint stress.

Experimental Example 2

Combined Use of DL-PC and PO-PC Improves Stress-Induced Memory Disorders

To mice made to develop a depression state by a restraint stress for 4 days was orally administered DL-PC and PO-PC, or polyethylene glycol (PEG) for 3 days. A water maze test was performed, and the memory disorder improving effect by the combined use of DL-PC and PO-PC was examined by measuring the retention latency. As a positive control, mouse free of a restraint stress was used and, as a negative control, PEG was used. The mice were administered with PEG or DL-PC and PO-PC by using an oral gavage needle.

Figure 2:
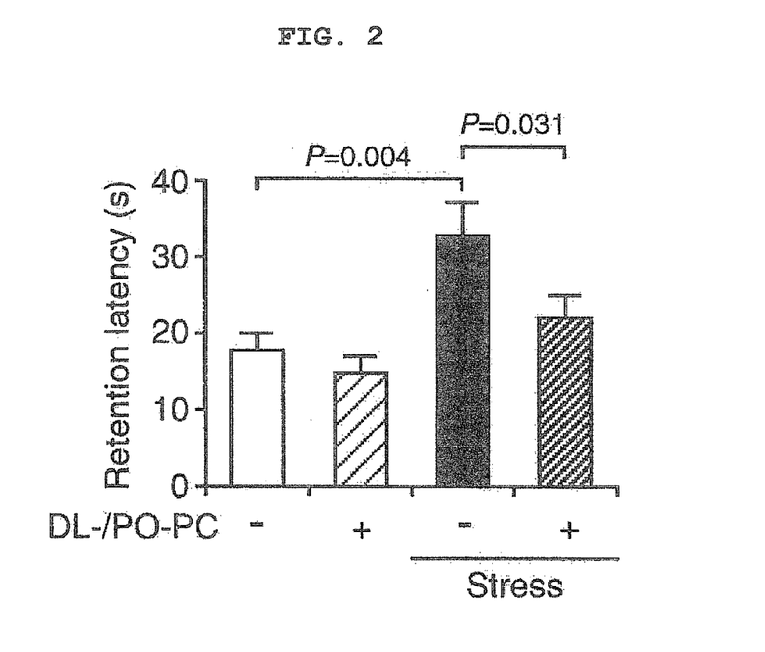
FIG. 2 is a graph showing that the combined administration of DL-PC and PO-PC improves stress-induced memory disorders. A restraint stress was loaded for 4 days, after which DL-PC and PO-PC, or polyethylene glycol (PEG) was orally administered for 3 days, and a water maze test was performed. In the graph, each column shows mean value (±SEM) of retention latency (n=8 in each experiment). P value, Dunnett's test. DL-/PO-PC: DL-PC and PO-PC

The results are shown in FIG. 2. The stress significantly prolonged the retention latency. The results show that a stress can induce memory disorders (memory disorders associated with depression). The combined use of DL-PC and PO-PC significantly improved extension of stress-induced retention latency. The results mean that the combined use of DL-PC and PO-PC has an action to improve stress-induced memory disorders (memory disorders associated with depression).

The combined use of DL-PC and PO-PC did not influence the memory function free of stress (namely, not in a depression state).

Figure 3:
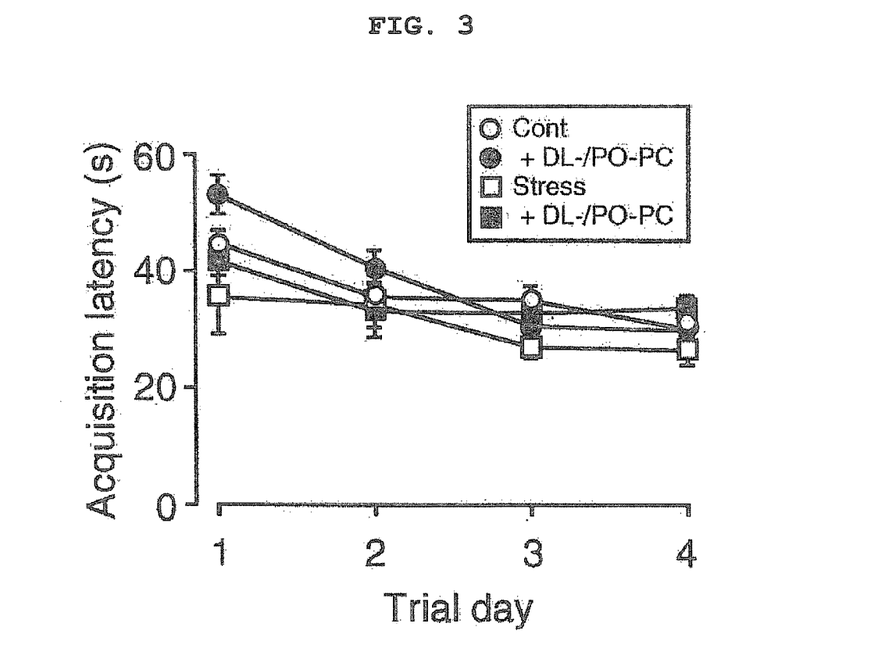
FIG. 3 is a graph showing that the combined administration of DL-PC and PO-PC does not influence acquisition latency. A restraint stress was loaded for 4 days, after which DL-PC and PO-PC, or polyethylene glycol (PEG) was orally administered for 3 days, and a forced swimming test was performed. In the graph, each column shows mean value (±SEM) of acquisition latency (n=8 in each experiment). P value, Dunnett's test. DL-/PO-PC: DL-PC and PO-PC

On the other hand, a stress did not influence acquisition latency, and the combined use of DL-PC and PO-PC did not influence the acquisition latency irrespective of the presence or absence of a stress (FIG. 3).

Experimental Example 3

Combined Use of DL-PC and PO-PC Recovers Stress-Induced Dephosphorylation of GSK-3β at Ser9 (Suppression of Stress-Induced GSK-3β Activation)

To mice made to develop a depression state by a restraint stress for 4 days was orally administered DL-PC and PO-PC, or polyethylene glycol (PEG) for 3 days. A forced swimming test was performed, hypothalamus was isolated, and a sample was prepared. Phosphorylation of Gsk-3β was examined by Western blotting. As a positive control, mouse free of a restraint stress was used and, as a negative control, PEG was used.

The mice loaded with a restraint stress and the mice not loaded with a restraint stress were orally administered with DL-PC and PO-PC once per day by using an oral gavage needle.

[Administration Protocol]
Combined use of DL-PC and PO-PC [DL-PC (0.05 mg/kg)+ PO-PC (0.05 mg/kg), 0.1 mg/kg as PC]

Figure 4:
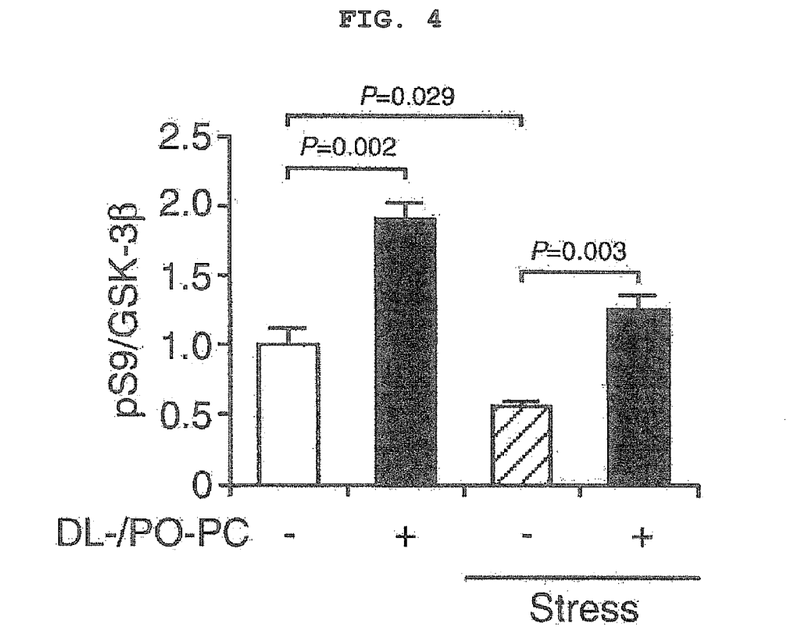

The results are shown in FIG. 4. It was confirmed that loading of a restraint stress dephosphorylates GSK-3β (namely, GSK-3β is activated), and the combined use of DL-PC and PO-PC improves dephosphorylation (namely, GSK-3β is deactivated). These results indicate that a stress dephosphorylates GSK-3β (activation of GSK-3β), and the combined use of DL-PC and PO-PC improves dephosphorylation of GSK-3β (inactivation of GSK-3β). Activation of GSK-3β is considered to exacerbate the depression state, and the combined use of DL-PC and PO-PC is suggested to have a possibility of improving depression by inactivation of GSK-3β

Experimental Example 4

Combined Use of DL-PC and PO-PC Improves Stress-Induced Dephosphorylation of Akt in Ser473 (Improvement of Stress-Induced Suppression of Akt Activation)

To mice made to develop a depression state by a restraint stress for 4 days was orally administered DL-PC and PO-PC, or polyethylene glycol (PEG) for 3 days. A forced swimming test was performed, hypothalamus was isolated, and a sample was prepared. Phosphorylation of Akt was examined by Western blotting. As a positive control, mouse free of a restraint stress was used and, as a negative control, PEG was used.

The mice loaded with a restraint stress and the mice not loaded with a restraint stress were orally administered with DL-PC and PO-PC once per day by using an oral gavage needle.

[Administration Protocol]
Combined use of DL-PC and PO-PC [DL-PC (0.05 mg/kg)+ PO-PC (0.05 mg/kg), 0.1 mg/kg as PC]

Figure 5:
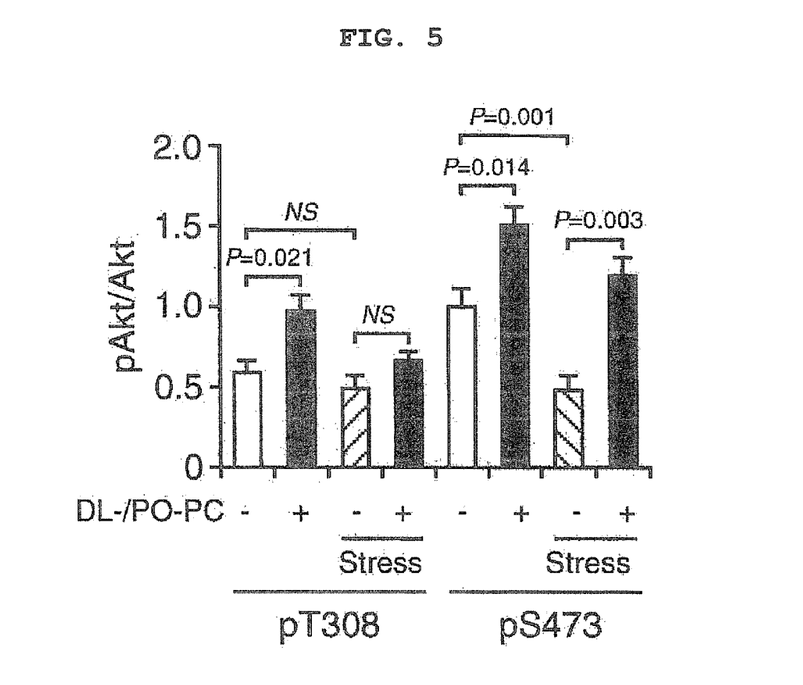

The results are shown in FIG. 5. The signal intensity of pT308 or pS473 was normalized by the intensity of total Akt.

It was confirmed that loading of a restraint stress dephosphorylates Akt (namely, suppression of Akt activation), but the combined use of DL-PC and PO-PC improves dephosphorylation (namely, suppression of Akt activation is improved). Since Akt is known to be inactivated by phosphorylation of GSK-3β, the combined use of DL-PC and PO-PC is considered to improve suppression of Akt activation and contribute to the phosphorylation of GSK-3β (inactivation of GSK-3β).

INDUSTRIAL APPLICABILITY

The combined use of DL-PC and PO-PC affords an action to improve stress-induced suppression of Akt activation and an action to suppress stress-induced GSK-3β activation, and is useful as various reagents (agents) for study based on the actions thereof, as well as an antidepressant and an agent for improving cognitive function associated with depression.

This application is based on a patent application No. 2013-214475 filed in Japan (filing date: Oct. 15, 2013), the contents of which are incorporated in full herein.

The invention claimed is:

1. A method of treating depression in a target comprising administering an effective amount of 1,2-dilinoleoyl-sn-glycero-3-phosphocholine and an effective amount of 1-palmitoyl-2-oleoyl-sn-glycero-3-phosphocholine in combination to a target in need thereof.

2. A method according to claim 1, wherein stress-induced GSK-3β activation is suppressed.

3. A method of treating depression in a target comprising administering an effective amount of 1,2-dilinoleoyl-sn-glycero-3-phosphocholine and 1-palmitoyl-2-oleoyl-sn-glycero-3-phosphocholine in combination to a target in need thereof, wherein
the level of Akt activation suppression is decreased relative to Akt activation suppression in the absence of administering 1,2-dilinoleoyl-sn-glycero-3-phosphocholine and 1-palmitoyl-2-oleoyl-sn-glycero-3-phosphocholine.

4. The method according to claim 3, wherein stress-induced GSK-3β activation is suppressed.

* * * * *